United States Patent
Hsiao et al.

(10) Patent No.: US 11,571,491 B2
(45) Date of Patent: *Feb. 7, 2023

(54) HYDROGEL WOUND DRESSING AND METHOD OF PREPARING THE SAME

(71) Applicant: TRONJEN MEDICAL TECHNOLOGY INC., Taichung (TW)

(72) Inventors: Hung-Kai Hsiao, Taichung (TW); Szu-Hsien Chen, Taichung (TW); Ya-Wen Ku, Taichung (TW); Ren-Shian Wang, Taichung (TW); Chiu-Fang Chen, Taichung (TW)

(73) Assignee: TRONJEN MEDICAL TECHNOLOGY INC., Taichung (TW)

( * ) Notice: Subject to any disclaimer, the term of this patent is extended or adjusted under 35 U.S.C. 154(b) by 665 days.

This patent is subject to a terminal disclaimer.

(21) Appl. No.: 16/656,636

(22) Filed: Oct. 18, 2019

(65) Prior Publication Data

US 2021/0023256 A1    Jan. 28, 2021

(30) Foreign Application Priority Data

Jul. 22, 2019 (TW) .................................. 108125783

(51) Int. Cl.
*A61L 15/60* (2006.01)
*A61L 15/20* (2006.01)
*A61L 15/26* (2006.01)
*A61L 26/00* (2006.01)

(52) U.S. Cl.
CPC ............... *A61L 15/60* (2013.01); *A61L 15/20* (2013.01); *A61L 15/26* (2013.01)

(58) Field of Classification Search
None
See application file for complete search history.

(56) References Cited

U.S. PATENT DOCUMENTS

| | | | | |
|---|---|---|---|---|
| 4,789,720 A | * | 12/1988 | Teffenhart | A61K 9/4891 528/76 |
| 2006/0142529 A1 | * | 6/2006 | Thiede | C08G 18/10 528/44 |
| 2009/0018480 A1 | * | 1/2009 | Mager | A61L 15/425 521/159 |

* cited by examiner

*Primary Examiner* — Kyung S Chang
(74) *Attorney, Agent, or Firm* — Hamre, Schumann, Mueller & Larson, P.C.

(57) ABSTRACT

Disclosed herein is a hydrogel wound dressing produced by the steps of a) providing an hydrophobic polyol which has six hydroxyl groups, b) providing an hydrophilic diisocyanate obtained by reacting a second diisocyanate with a hydrophilic polyether diol, c) reacting the hydrophobic polyol with the hydrophilic diisocyanate to obtain a first prepolymer which includes 3 to 6 isocyanate groups, d) partially crosslinking the first prepolymer using a crosslinking agent to obtain a second prepolymer, and e) subjecting the second prepolymer to an end-capping reaction with a silane-containing compound to obtain the hydrogel wound dressing.

11 Claims, No Drawings

HYDROGEL WOUND DRESSING AND METHOD OF PREPARING THE SAME

CROSS-REFERENCE TO RELATED APPLICATION

This application claims priority of Taiwanese Patent Application No. 108125783, filed on Jul. 22, 2019.

FIELD

The disclosure relates to a hydrogel wound dressing and a method of preparing the same. In particular, the hydrogel wound dressing is suitable for contact with open wounds, facilitating optimal wound healing.

BACKGROUND

Wound dressings have been used to promote healing, to protect damaged tissues from contamination by dirt and foreign substances, and to protect against infection. Hydrogel dressings, silicone gel dressings, and polyurethane (PU) dressings are the most commonly used dressings in wound care. However, the silicone gel dressings have low vapor permeability (their water vapor transmission rate is usually less than 400 g/m2/day), and thus may cause wound infiltration and allergy. Furthermore, the polyurethane dressings have no significant effect on reducing scar formation.

Hydrogel wound dressings have several advantages over other wound dressings. Hydrogel polymers are hydrophilic, so that they absorb water and keep the environment moist, thereby promoting healing, rehydrating dead tissues, and enhancing autolytic debridement. In addition, the hydrogel dressings are often cool on the surface of the wound, helping to relieve pain. However, there are problems with conventional hydrogel wound dressings. Some conventional hydrogel wound dressings have been found to lack sufficient mechanical strength, causing the wound dressing to shed, and sometimes to tear. Such conventional hydrogel dressings are unable to absorb sufficient wound exudates, leading to proliferation of bacteria.

In view of the foregoing, the applicants attempted to develop a new hydrogel wound dressing, which is antimicrobial and has high clinical efficiency.

SUMMARY

Accordingly, in a first aspect, the present disclosure provides a hydrogel wound dressing produced by the steps of:
a). providing a hydrophobic polyol which has six hydroxyl groups, and which is obtained by:
  a-1) reacting a branched triol with a first diisocyanate to obtain triisocyanate intermediate, and
  a-2) reacting the triisocyanate intermediate with a hydrophobic polyether triol;
b). providing a hydrophilic diisocyanate obtained by reacting a second diisocyanate with a hydrophilic polyether diol;
c). reacting the hydrophobic polyol with the hydrophilic diisocyanate to obtain a first prepolymer which includes 3 to 6 isocyanate groups;
d). partially crosslinking the first prepolymer using a crosslinking agent to obtain a second prepolymer; and
e). subjecting the second prepolymer to an end-capping reaction with a silane-containing compound to obtain the hydrogel wound dressing.

In a second aspect, the present disclosure provides a process for producing a hydrogel wound dressing, comprising the steps of:
a). providing a hydrophobic polyol which has six hydroxyl groups, and which is obtained by:
  a-1) reacting a branched triol with a first diisocyanate to obtain a triisocyanate intermediate, and
  a-2) reacting the triisocyanate intermediate with a hydrophobic polyether triol;
b). providing a hydrophilic diisocyanate obtained by reacting a second diisocyanate with a hydrophilic polyether diol;
c). reacting the hydrophobic polyol with the hydrophilic diisocyanate to obtain a first prepolymer which includes 3 to 6 isocyanate groups;
d). partially crosslinking the first prepolymer using a crosslinking agent to obtain a second prepolymer; and
e). subjecting the second prepolymer to an end-capping reaction with a silane-containing compound to obtain the hydrogel wound dressing.

DETAILED DESCRIPTION

It is to be understood that, if any prior art publication is referred to herein, such reference does not constitute an admission that the publication forms a part of the common general knowledge in the art, in Taiwan or any other country.

For the purpose of this specification, it will be clearly understood that the word "comprising" means "including but not limited to", and that the word "comprises" has a corresponding meaning.

Unless defined otherwise, all technical and scientific terms used herein have the meaning commonly understood by a person skilled in the art to which the present disclosure belongs. One skilled in the art will recognize many methods and materials similar or equivalent to those described herein, which could be used in the practice of the present disclosure. Indeed, the present disclosure is in no way limited to the methods and materials described.

The present disclosure provides a hydrogel wound dressing produced by the steps of:
a). providing a hydrophobic polyol which has six hydroxyl groups, and which is obtained by:
  a-1) reacting a branched triol with a first diisocyanate to obtain a triisocyanate intermediate, and
  a-2) reacting the triisocyanate intermediate with a hydrophobic polyether triol;
b). providing a hydrophilic diisocyanate obtained by reacting a second diisocyanate with a hydrophilic polyether diol;
c). reacting the hydrophobic polyol with the hydrophilic diisocyanate to obtain a first prepolymer which includes 3 to 6 isocyanate groups;
d). partially crosslinking the first prepolymer using a crosslinking agent to obtain a second prepolymer; and
e). subjecting the second prepolymer to an end-capping reaction with a silane-containing compound to obtain the hydrogel wound dressing.

According to the present disclosure, the branched triol is selected from the group consisting of 1,1,1-trimethylolpropane (TMP), triethanolamine, glycerol, 1,2,6-hexanetriol, 1,2,4-butanetriol, glycerol ethoxylate, and combinations thereof.

According to the present disclosure, the first diisocyanate and the second diisocyanate are independently selected from the group consisting of hexamethylene diisocyanate (HDI), methylene dicyclohexyl diisocyanate (H12MDI), isophorone diisocyanate (IPDI), and combinations thereof.

According to the present disclosure, the hydrophobic polyether triol is selected from the group consisting of polypropylene glycol) triol, poly(tetramethylene ether) glycol triol, and a combination thereof.

According to the present disclosure, the hydrophilic polyether diol is polyethylene glycol.

According to the present disclosure, the crosslinking agent is a polyether diamine crosslinking agent selected from the group consisting of polyethylene glycol diamine, polypropylene glycol diamine, and a combination thereof.

According to the present disclosure, the crosslinking agent is in an amount greater than 0 molar part and not greater than 0.4 molar part based on 2 molar parts of the first prepolymer.

According to the present disclosure, the second prepolymer has a weight-average molecular weight less than 200,000 g/mol. In an exemplary embodiment, the weight-average molecular weight of the second prepolymer ranges from 30,000 g/mol to 60,000 g/mol.

Specifically, the applicants found that when the crosslinking agent is in an amount greater than 0.4 molar part based on 2 molar parts of the first prepolymer, the weight average molecular weight of the obtained second prepolymer could be increased, thereby causing the finally obtained hydrogel wound dressing to have lower viscosity.

According to the present disclosure, the silane-containing compound is an aminosilane compound selected from the group consisting of aminoalkyl alkoxysilane, aminoalkyl trialkylsilane, and a combination thereof.

In certain embodiments, the aminosilane compound is selected from the group consisting of (3-aminopropyl)triethoxysilane (APTES), (3-aminopropyl)trimethoxysilane (APTMS), (3-aminopropyl)diethoxymethylsilane (APDEMS), and combinations thereof.

According to the present disclosure, the applicants observed, via a microscopic scale measurement or a mesoscopic scale measurement, that the hydrophobic region, which is formed by the hydrophobic polyol and is located inside the first prepolymer, and the hydrophilic region, which is formed by the hydrophilic diisocyanate and is located outside the first prepolymer, are in a state of phase separation. This property causes the hydrogel wound dressing to be in a state of microphase separation, thereby facilitating the formation of tiny holes through which water vapor can penetrate.

The disclosure will be further described by way of the following examples. However, it should be understood that the following examples are solely intended for the purpose of illustration and should not be construed as limiting the disclosure in practice.

EXAMPLES

Example 1. Preparation of Hydrogel Wound Dressing of Present Disclosure

The hydrogel wound dressing of the present disclosure was prepared as follows.

In step (a1), 1,1,1-trimethylolpropane (TMP) and hexamethylene diisocyanate (HDI) were mixed in a molar ratio of 1:3, and 0.05 wt % triethylenediamine (TEDA) (based on the total weight of TMP and HDI) was then used as a catalyst. The resultant mixture was stirred at 80° C. for 90 minutes under an enclosed nitrogen atmosphere. During the reaction above, fourier transform-infrared (FT-IR) spectroscopy analysis was used to monitor the presence of the characteristic NCO group (—NCO) peak at 2270 cm$^{-1}$. The characteristic NCO group peak at 2270 cm$^{-1}$ was detected, indicating that a triisocyanate intermediate was obtained.

In step (a2), the triisocyanate intermediate and poly (propylene glycol) triol (PPG 4000 triol) were mixed in a molar ratio of 1:3, and 0.05 wt % TEDA (based on the total weight of the triisocyanate intermediate and PPG 4000 triol) was then used as a catalyst. The resultant mixture was stirred at 80° C. for 90 minutes under an enclosed nitrogen atmosphere. During the reaction above, FT-IA spectroscopy analysis was performed as described in step (a1). The characteristic NCO group peak at 2270 cm$^{-1}$ was not detected, indicating that a hydrophobic polyol which has six hydroxyl groups was obtained.

In step (b), poly(ethylene glycol) diol (PEG 1000 diol) and HDI were mixed in a molar ratio of 1:2, and 0.05 wt % TEDA (based on the total weight of PEG 1000 diol and HDI) was then used as a catalyst. The resultant mixture was stirred at 80° C. for 90 minutes under an enclosed nitrogen atmosphere. During the reaction above, FT-IR spectroscopy analysis was performed as described in step (a1). The characteristic NCO group peak at 2270 cm$^{-1}$ was detected, indicating that a hydrophilic diisocyanate was obtained.

In step (c), the hydrophobic polyol and the hydrophilic diisocyanate were mixed in a molar ratio of 1:6, followed by stirring at 80° C. for 90 minutes under an enclosed nitrogen atmosphere. During the reaction above, FT-IR spectroscopy analysis was performed as described in step (a1). The characteristic NCO group peak at 2270 cm$^{-1}$ was detected, indicating that a first prepolymer which included 6 isocyanate groups was obtained. The first prepolymer had a hydrophobic interior and a hydrophilic exterior.

In step (d), the first prepolymer and polyethylene glycol diamine (PEG diamine 5000, acting as a crosslinking agent) were mixed in a molar ratio of 2:0.2, followed by stirring at 80° C. for 90 minutes under an enclosed nitrogen atmosphere. During the cross-linking reaction above, FT-IR spectroscopy analysis was performed as described in step (a1). The characteristic NCO group peak at 2270 cm was detected, indicating that a second prepolymer which included several isocyanate groups was obtained. The second prepolymer had a weight average molecular weight of 52,000 g/mol.

In step (e) the second prepolymer and (3-aminopropyl) triethoxysilane (APTES) were mixed in a molar ratio of 1:0.8, followed by stirring at 80° C. for 90 minutes under an enclosed nitrogen atmosphere. During the end-capping reaction above, FT-IR spectroscopy analysis was performed as described in step (a1). The characteristic NCO group peak at 2270 cm$^{-1}$ was not detected, indicating that an APTES-end-capped polyurethane (PU) hydrogel was obtained.

The APTES-end-capped PU hydrogel thus obtained was coated into a hydrogel wound dressing patch having a thickness of 0.6 mm by a coater. The resultant hydrogel wound dressing patch was used for the following example.

Example 2. Measurement of Water Vapor Transmission Rate (MVTR)

The water vapor transmission rate of the hydrogel wound dressing patch of the present disclosure was measured according to DIN EN 13726-2: 2002-MVTR. The experimental result showed that the hydrogel wound dressing patch had a MVTR of 800 g/m$^2$/day, thus indicating that the hydrogel wound dressing patch of the present disclosure has good vapor permeability and moisture retention, and hence can avoid wound infiltration.

Example 3. Peel Strength Testing

The peel strength of the hydrogel wound dressing patch of the present disclosure was measured according to ASTM D3330-2017. The experimental result showed that the hydrogel wound dressing patch had a peel strength of 450 g/25 mm, thus indicating that the hydrogel wound dressing patch of the present disclosure can adhere properly to the skin and will not cause significant pain during stripping.

Example 4. Ultraviolet (UV) Light Penetration Rate

The UV light penetration rate of the hydrogel wound dressing patch of the present disclosure was determined at a wavelength of 380 nm according to the technique well known to and routinely used by one skilled in the art. The experimental result showed that the UV light penetration rate of the hydrogel wound dressing patch was 8%, thus indicating that the hydrogel wound dressing patch of the present disclosure can effectively block the penetration of UV light and thereby reduce hyperpigmentation.

Example 5. Antimicrobial Test

Pieces of the hydrogel wound dressing patch of the present disclosure (which had a size of 1 cm×1 cm and a weight of 0.6 g) and pieces of a commercially available gauze (which had a size of 5 cm×5 cm and a weight of 0.6 g) were sterilized by gamma rays (15-20 kGy) for serving as test samples. The pieces of the hydrogel wound dressing patch and the pieces of the gauze were respectively added to bacterial broths of *Escherichia coli* (*E. coli*, ATCC 35218), *Pseudomonas aeruginosa* (*P. aeruginosa*, ATCC 27853), and *Staphylococcus aureus* (*S. aureus*, ATCC 25923). Each of the three bacterial broths contained a concentration of bacteria that approximated the 0.5 McFarland standard turbidity, and was prepared using a iris-buffered saline (TBS) (containing 20 mM Tris, 150 mM NaCl, and 0.05% Tween-20 (pH 7.4)). The respective broth with the corresponding test sample was incubated in a thermostatic shaking incubator (37° C., 220 rpm) for 2 hours.

Subsequently, the resultant bacterial suspension of each cultured broth was collected and then subjected to turbidimetry. The approximate concentration of the bacteria in the suspension was determined by Mcfarland turbidity standards. In addition, for the sake of comparison, each of the three bacterial broths before incubation, which contained no hydrogel wound dressing patch or gauze, was subjected to the same turbidimetry. The result is shown in Table 1 below.

TABLE 1

| Bacterial species | Bacterial concentration before incubation (cfu/mL) | Bacterial concentration after incubation with hydrogel wound dressing patch (cfu/mL) | Bacterial concentration after incubation with gauze (cfu/mL) |
|---|---|---|---|
| E. coli | $10^{6.50}$ | $10^{5.16}$ | $10^{6.31}$ |
| P. aeruginosa | $10^{6.32}$ | $10^{4.55}$ | $10^{5.99}$ |
| S. aureus | $10^{6.40}$ | $10^{5.09}$ | $10^{5.98}$ |

As shown in Table 1, as compared to the bacterial concentration before incubation (i.e., the original bacterial concentration of the corresponding one of the three bacterial broths), after incubation with the hydrogel wound dressing patch of the present disclosure, the bacterial concentration of each of the three bacterial suspensions obtained from the cultured broths was significantly decreased. In contrast, after incubation with the gauze, the bacterial concentration of each of the three bacterial suspensions obtained from the cultured broths was not significantly decreased.

This result indicated that the hydrogel wound dressing patch of the present disclosure is effective in inhibiting the growth of bacteria (such as *E. coli*, *P. aeruginosa*, and *S. aureus*).

Example 6. Wound Healing Assay

A. Test Animals

Nulliparous female Sprague Dawley (S.D.) rats (5-12 weeks old, body weight>120 g) were purchased from Laboratory Animal Center, National Cheng Kung University. The S.D. rats were kept in an animal room with an independent air conditioning system under the following laboratory conditions: a temperature of 22±3° C. and a relative humidity of 30-70%. Furthermore, water and feed were provided ad libitum for all experimental animals.

B. Test Materials

Pieces of the hydrogel wound dressing patch of the present disclosure (which had a size of 3 cm (width)×3 cm (length)×0.5 mm (thickness)), pieces of CICA-CARE silicone gel sheet (Smith & Nephew Co., Ltd., Australia) (which had a size of 3 cm (width)×3 cm (length)), and pieces of PU hydrogel wound dressing patch (TAICEND Co., Ltd., Taiwan) (which had a size of 3 cm (width)×3 cm (length)) were sterilized by gamma rays (15-20 kGy) and were used for the following experiment.

C. Experimental Procedures:

S.D. rats were divided into 3 groups, including one experimental group and two comparative groups (i.e., comparative groups 1 and 2) (n=12 for each group). The dosal part of each S.D. rat was shaved and then disinfected with 75% alcohol. Thereafter, the S.D. rats were anesthetized with isoflurane, followed by cutting to form a skin wound having an area of about 2 cm×2 cm on the back of the respective S.D. rat using sterile surgical scissors and a blade.

The skin wounds of the experimental group, the comparative group 1 and the comparative group 2 were respectively applied with the sterilized hydrogel wound dressing patch of the present disclosure, CICA-CARE silicone gel sheet, and PU hydrogel wound dressing patch described in section B of this example, followed by fixing the dressing patch or sheet with breathable elastic bandages.

On Day 7, Day 14, and Day 21 after application of the dressing patch or sheet, three S.D. rats were taken from each group and their skin wounds were photographed using a digital camera. The three rats of each group were then discarded from the experiment. For the other S.D. rats in each group, the respective skin wound was treated with a new dressing patch or sheet as described above, and the respective wound area was calculated by ImageJ software.

Moreover, on Day 24 after application of the dressing patch or sheet, the remaining three S.D. rats in each group were subjected to scar assessment using Vancouver Scar Scale (VSS). The VSS characterizes scars by their pigmentation, vascularity, pliability, and height. The resemblance to normal skin has the score of 0, while a greater score indicates a greater pathologic condition of the scar.

D. Results:

The wound areas determined in the S.D. rats are shown in Table 2. It can be seen from Table 2 that, on Day 21 after application of the dressing patch or sheet, the wound area of the experimental group was significantly lower than those of the comparative groups 1 and 2, indicating that the hydrogel wound dressing patch of the present disclosure can effectively promote wound healing.

TABLE 2

|  | Experimental group | Comparative group 1 | Comparative group 2 |
|---|---|---|---|
|  |  | Wound area (cm²) |  |
| Day 7 | 1.05 ± 0.23 | 2.1 ± 0.34 | 2.2 ± 0.43 |
| Day 14 | 0.56 ± 0.41 | 1.39 ± 0.31 | 0.98 ± 0.41 |
| Day 21 | 0.2 ± 0.03 | 0.9 ± 0.05 | 0.92 ± 0.61 |

The score results of the assessment of scar characteristics are shown in Table 3. It can be seen from Table 3 that the pigmentation, vascularity, pliability, and height scores of the experimental group were significantly lower than those of the comparative groups 1 and 2, indicating that the hydrogel wound dressing patch of the present disclosure can effectively prevent scarring.

TABLE 3

| Characteristics analyzed | Experimental group | Comparative group 1 | Comparative group 2 |
|---|---|---|---|
| Pigmentation | 1 | 3 | 2.3 |
| Pliability | 1.3 | 2.7 | 2.3 |
| Height | 0 | 1 | 1.3 |
| Vascularity | 1.3 | 2 | 2 |

Summarizing the above test results, it is clear that the hydrogel wound dressing patch of the present disclosure has satisfactory vapor permeability, moisture retention, and peel strength, and can effectively block the penetration of UV light and thereby reduce hyperpigmentation. In addition, the hydrogel wound dressing patch of the present disclosure can effectively inhibit the growth of bacteria, promote wound healing, and prevent scarring.

All patents and references cited in this specification incorporated herein in their entirety as reference. Where there is conflict, the descriptions in this case, including the definitions, shall prevail.

While the disclosure has been described in connection with what are considered the exemplary embodiments, it is understood that this disclosure is not limited to the disclosed embodiments but is intended to cover various arrangements included within the spirit and scope of the broadest interpretation so as to encompass all such modifications and equivalent arrangements.

What is claimed is:

1. A process for producing a hydrogel wound dressing, comprising the steps of:
   a) providing a hydrophobic polyol which has six hydroxyl groups, and which is obtained by:
      i. a-1) reacting a branched triol with a first diisocyanate to obtain a triisocyanate intermediate, and
      ii. a-2) reacting the triisocyanate intermediate with a hydrophobic polyether triol;
   b) providing a hydrophilic diisocyanate obtained by reacting a second diisocyanate with a hydrophilic polyether diol;
   c) reacting the hydrophobic polyol with the hydrophilic diisocyanate to obtain a first prepolymer which includes 3 to 6 isocyanate groups;
   d) partially crosslinking the first prepolymer using a crosslinking agent to obtain a second prepolymer; and
   e) subjecting the second prepolymer to an end-capping reaction with a silane-containing compound to obtain the hydrogel wound dressing.

2. The process according to claim 1, wherein the branched triol is selected from the group consisting of trimethylolpropane, triethanolamine, glycerol, 1,2,6-hexanetriol, 1,2,4-butanetriol, glycerol ethoxylate, and combinations thereof.

3. The process according to claim 1, wherein the first diisocyanate and the second diisocyanate are independently selected from the group consisting of hexamethylene diisocyanate, methylene dicyclohexyl diisocyanate, isophorone diisocyanate, and combinations thereof.

4. The process to claim 1, wherein the hydrophobic polyether triol is selected from the group consisting of polypropylene glycol triol, poly(tetramethylene ether) glycol triol, and a combination thereof.

5. The process according to claim 1, wherein the hydrophilic polyether diol is polyethylene glycol.

6. The process according to claim 1, wherein the crosslinking agent is a polyether diamine crosslinking agent.

7. The process according to claim 6, wherein the polyether diamine crosslinking agent is selected from the group consisting of polyethylene glycol diamine, polypropylene glycol diamine, and a combination thereof.

8. The process according to claim 1, wherein the crosslinking agent is in an amount greater than 0 molar part and not greater than 0.4 molar part based on 2 molar parts of the first prepolymer.

9. The process according to claim 8, wherein the second prepolymer has a weight-average molecular weight less than 200,000 g/mol.

10. The process according to claim 9, wherein the weight-average molecular weight of the second prepolymer ranges from 30,000 g/mol to 60,000 g/mol.

11. The process according to claim 1, wherein the silane-containing compound is an aminosilane compound.

\* \* \* \* \*